(12) United States Patent
Lee

(10) Patent No.: US 10,780,193 B2
(45) Date of Patent: Sep. 22, 2020

(54) ROTARY AROMATHERAPY LAMP STRUCTURE

(71) Applicant: Huan-Ping Lee, Toufen (TW)

(72) Inventor: Huan-Ping Lee, Toufen (TW)

( * ) Notice: Subject to any disclaimer, the term of this patent is extended or adjusted under 35 U.S.C. 154(b) by 78 days.

(21) Appl. No.: 16/164,808

(22) Filed: Oct. 19, 2018

(65) Prior Publication Data

US 2020/0121819 A1    Apr. 23, 2020

(51) Int. Cl.
| | |
|---|---|
| *A61L 9/03* | (2006.01) |
| *F21V 23/00* | (2015.01) |
| *F21V 1/10* | (2006.01) |
| *F21V 33/00* | (2006.01) |
| *A61M 21/02* | (2006.01) |
| *A61M 21/00* | (2006.01) |

(52) U.S. Cl.
CPC .............. *A61L 9/032* (2013.01); *A61M 21/02* (2013.01); *F21V 1/10* (2013.01); *F21V 23/005* (2013.01); *F21V 33/0024* (2013.01); *F21V 33/0056* (2013.01); *A61L 2209/12* (2013.01); *A61L 2209/15* (2013.01); *A61M 2021/0016* (2013.01); *A61M 2021/0055* (2013.01); *A61M 2021/0066* (2013.01)

(58) Field of Classification Search
CPC .......... A61L 9/032; F21V 23/005; F21V 1/10; F21V 33/0024; F21V 33/0056; A61M 2021/0016; A61M 21/02
See application file for complete search history.

(56) References Cited

U.S. PATENT DOCUMENTS

| | | | | |
|---|---|---|---|---|
| 5,309,338 A | * | 5/1994 | Liu | A61L 9/122 362/253 |
| 2018/0289169 A1 | * | 10/2018 | Le | A47C 21/044 |
| 2019/0247532 A1 | * | 8/2019 | Hsiao | B01F 3/04 |

FOREIGN PATENT DOCUMENTS

| | | | | |
|---|---|---|---|---|
| CN | 209371073 U | * | 9/2019 | |
| DE | 202018106239 U1 | * | 11/2018 | .......... F21V 33/0024 |

* cited by examiner

*Primary Examiner* — Joseph L Williams
(74) *Attorney, Agent, or Firm* — Leong C. Lei

(57) ABSTRACT

A rotary aromatherapy lamp structure includes an aromatherapy lamp and rotating cover. A base of the aromatherapy lamp is configured with a control circuit board in electric connection with a fan and heating element and first support, a part of the first support positioned relatively above the fan and heating element is in combination with a container, and the first support above the container is extended with a fulcrum; the rotating cover is covered on the fan, heating element and first support, and the fulcrum is used to prop against an axle center of the fan leaves, allowing a space to be formed between the rotating cover and base and thus allowing the rotating cover to have a rotation mechanism. Whereby, the heating element heats the container to speed the essential oil evaporation, and air flow generated from the fan blows the fan leaves to rotate the rotating cover.

10 Claims, 5 Drawing Sheets

500
ROTARY AROMATHERAPY LAMP STRUCTURE

(A) TECHNICAL FIELD OF THE INVENTION

The present invention relates to a rotary aromatherapy lamp structure, and more particularly to an aromatherapy lamp in combination with a rotating cover, using a heating element configured on the aromatherapy lamp to heat essential oil in a container to speed the evaporation thereof, and further using a fan configured on the aromatherapy lamp to generate air flow to blow fan leaves of the rotating cover, thereby allowing the rotating cover to have an automatic rotation function.

(B) DESCRIPTION OF THE PRIOR ART

With the continuous improvement of the quality of life, people are paying more and more attention to life on the material and spiritual level. To make the environment no special odor and turbid air to improve work efficiency or obtain a better spiritual state, some people places an air cleaner indoor to purify air or aromatics to eliminate odors in the room.

For general aromatics, they are placed in the room to provide home environment such as a bedroom, living room or toilet with a steady stream of aroma, and improve the quality of life at home. In addition, essential oils are also gradually loved by the masses of customers. The essential oil is heated a little to evaporate in the room, which not only can be used to eliminate indoor odor but allows people mind to be relaxed.

However, conventional air fresheners mainly accommodate a liquid or solid aromatic (such as perfume, essential oil or balm) in a container, and only allows the aromatic to evaporate spontaneously via through holes configured on the container, resulting in the aroma being incapable of spreading effectively to the whole room when a conventional air freshener is used. In addition, conventional aromatherapy lamps used to hold essential oil only can be used to heat the essential oil a little to make the volatile essential oil spread spontaneously; it is also impossible to effectively diffuse the fragrance into the entire indoor space when a conventional essential oil aromatherapy lamp is used.

SUMMARY OF THE INVENTION

The present invention proposes a rotary aromatherapy lamp structure, including: an aromatherapy lamp, including a base, control circuit board, fan, light-emitting element and first support, the control circuit board configured on the base and respectively in electric connection with the fan and light-emitting element, surfaces of the fan and base facing toward the same direction, allowing air flow generated from the fan to be blown above the surface of the base, the first support configured on the surface of the base, the first support configured with a mounting portion in combination with a container and positioned relatively above the fan and heating element, the first support further extended with a fulcrum positioned relatively above the container, and the heating element adjacent to a lower position of the container; and a rotating cover, being a hollow body and adapted to cover the base of the aromatherapy lamp, a top end of the rotating cover configured with fan leaves, and a bottom end thereof formed with an opening, a center of the leaves configured with an axle center, the rotating cover adapted to cover the fan, heating element and first support of the aromatherapy lamp, and the fulcrum of the first support adapted to prop against the axle portion of the fan, allowing a space to be formed between the rotating cover and base.

The present invention is characterized in that the fan leaves are configured on the top end of the rotating cover, and the fulcrum of the first support is used to prop against the axle center of the fan leaves, allowing a space to be formed between the rotating cover and aromatherapy lamp to make the rotating cover have a rotating mechanism. Therefore, essential oil is filled in the container of the aromatherapy lamp upon use, the heating element is used to heat the essential oil inside the container, allowing the essential oil to be volatilized, and the air flow generated from the fan is then used to blow the fan leaves of the rotating cover to make the rotating cover have an automatic rotation function, thereby increasing the flow amount of the air flow through the rotation of the fan leaves of the rotating cover to diffuse the volatilized essential oil to indoor space.

DETAILED DESCRIPTION OF THE PREFERRED EMBODIMENTS

Figure 1:
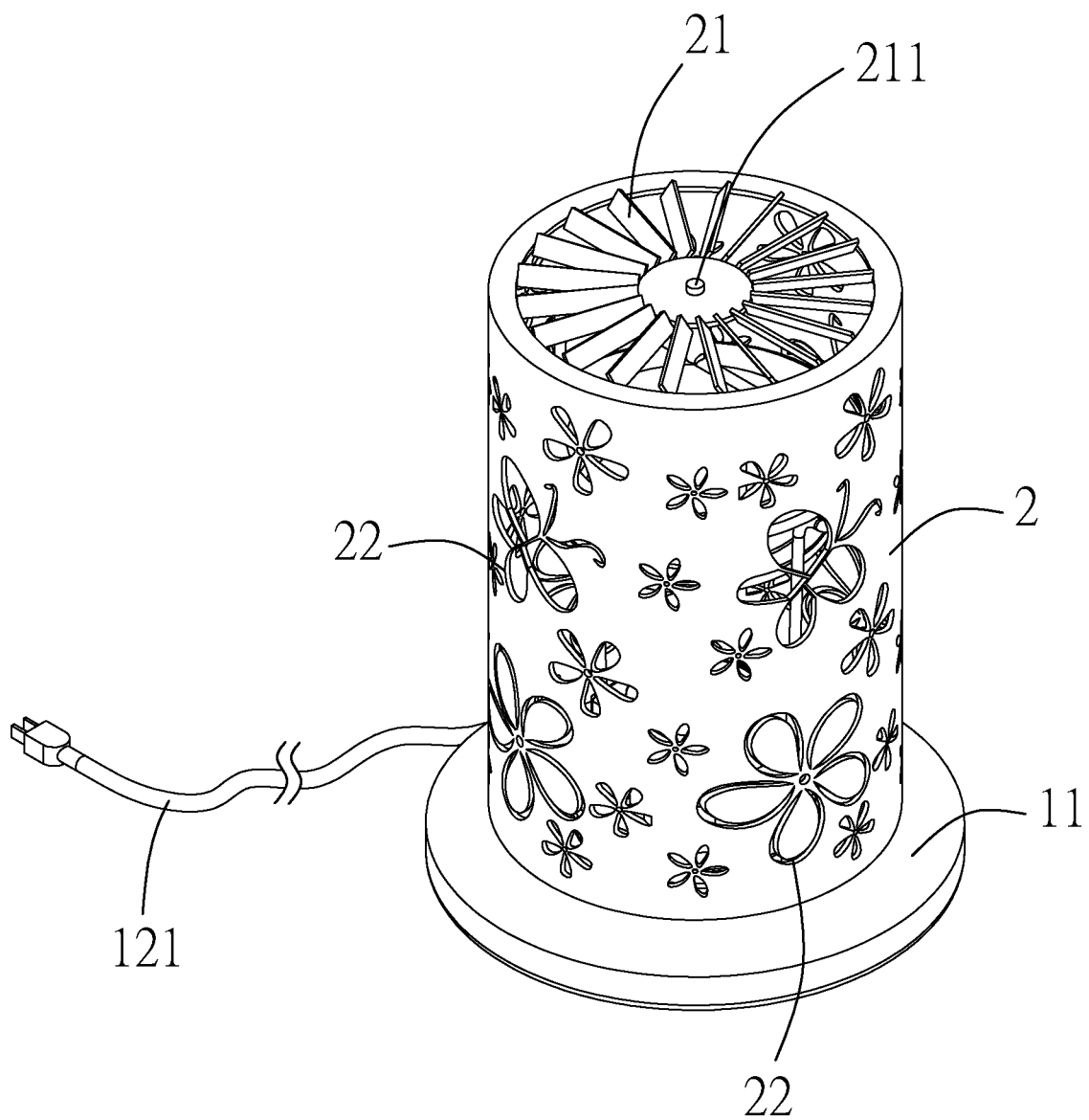
FIG. 1 is a perspective view of a rotary aromatherapy lamp structure of the present invention.
Figure 2:
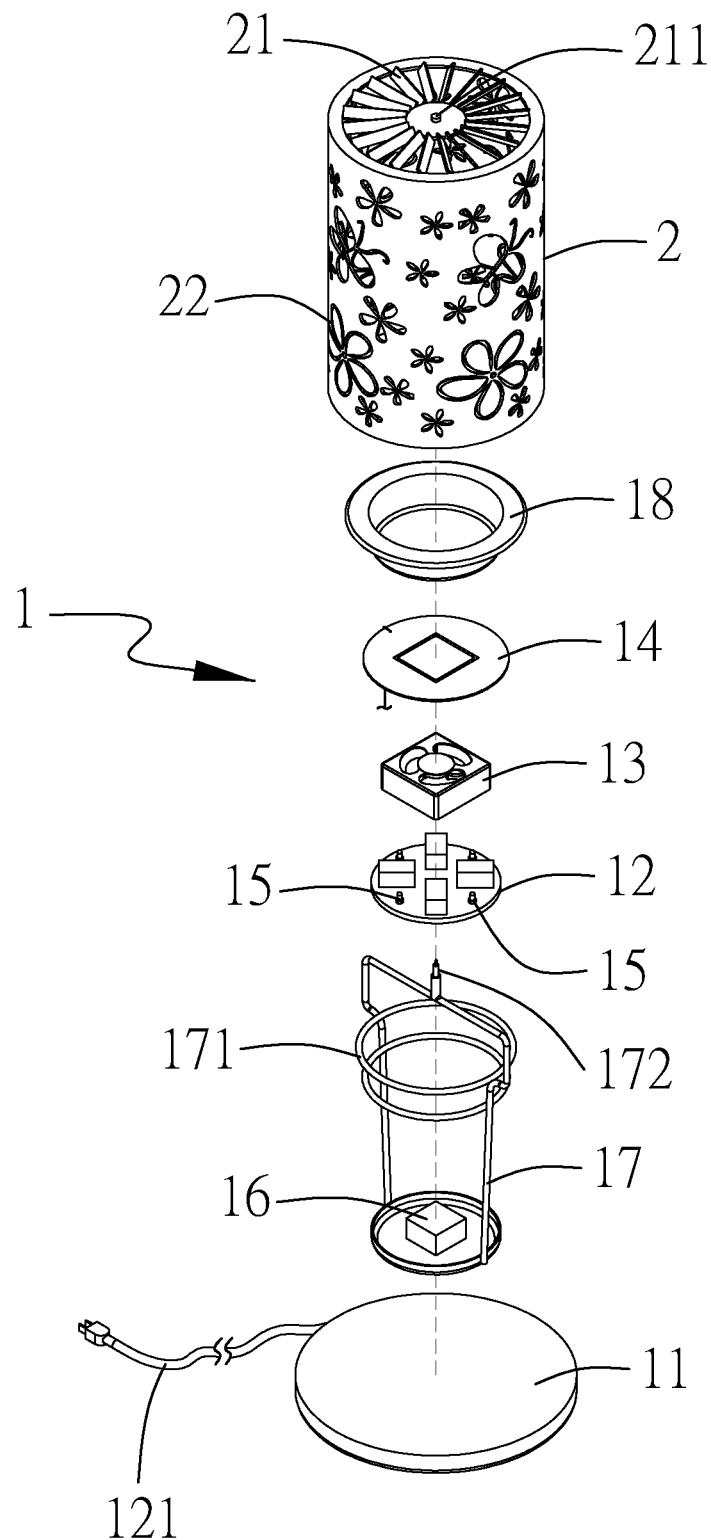
FIG. 2 is an exploded view of the rotary aromatherapy lamp structure of the present invention.

First, referring to FIGS. 1 to 4, a rotary aromatherapy lamp structure of the present invention includes an aromatherapy lamp 1 and rotating cover 2.

The aromatherapy lamp 1 includes a base 11, a control circuit board 12, a fan 13, a heating element 14, at least one light-emitting element 15, a spacer 16 and a first support 17, where the control circuit board 12 is configured on the base 11 and respectively in electric connection with the fan 13 and heating element 14. For example, the fan 13 may be positioned between the control circuit board 12 and heating element 14; the surfaces of the fan 13 and base 11 are faced in the same direction, allowing the air flow generated from the fan 13 to flow above the surface of the base 11; the spacer 16 may be configured on the bottom of the control circuit board 12; the first support 14 is configured with a mounting portion 171 which may be formed into an annular body and in combination with a container 18 made of glass or ceramics, where the container 18 is caused to align with the upper positions of the fan 13 and heating element 14; the heating element 14 may be touched with or adjacent to the bottom of the container 18; and the first support 17 is further extended with a fulcrum 172 positioned relatively above the container 18.

The light-emitting element 15 and control circuit board 12 are in electric connection with each other, for example, the light-emitting element 15 may be configured on the control circuit board 12 or other position. The control circuit board 12 is in electric connection with an electric wire 121 further in connection with mains and further respectively supplies power to the fan 13, heating element 14 and the at least one light-emitting element 15.

Figure 3:
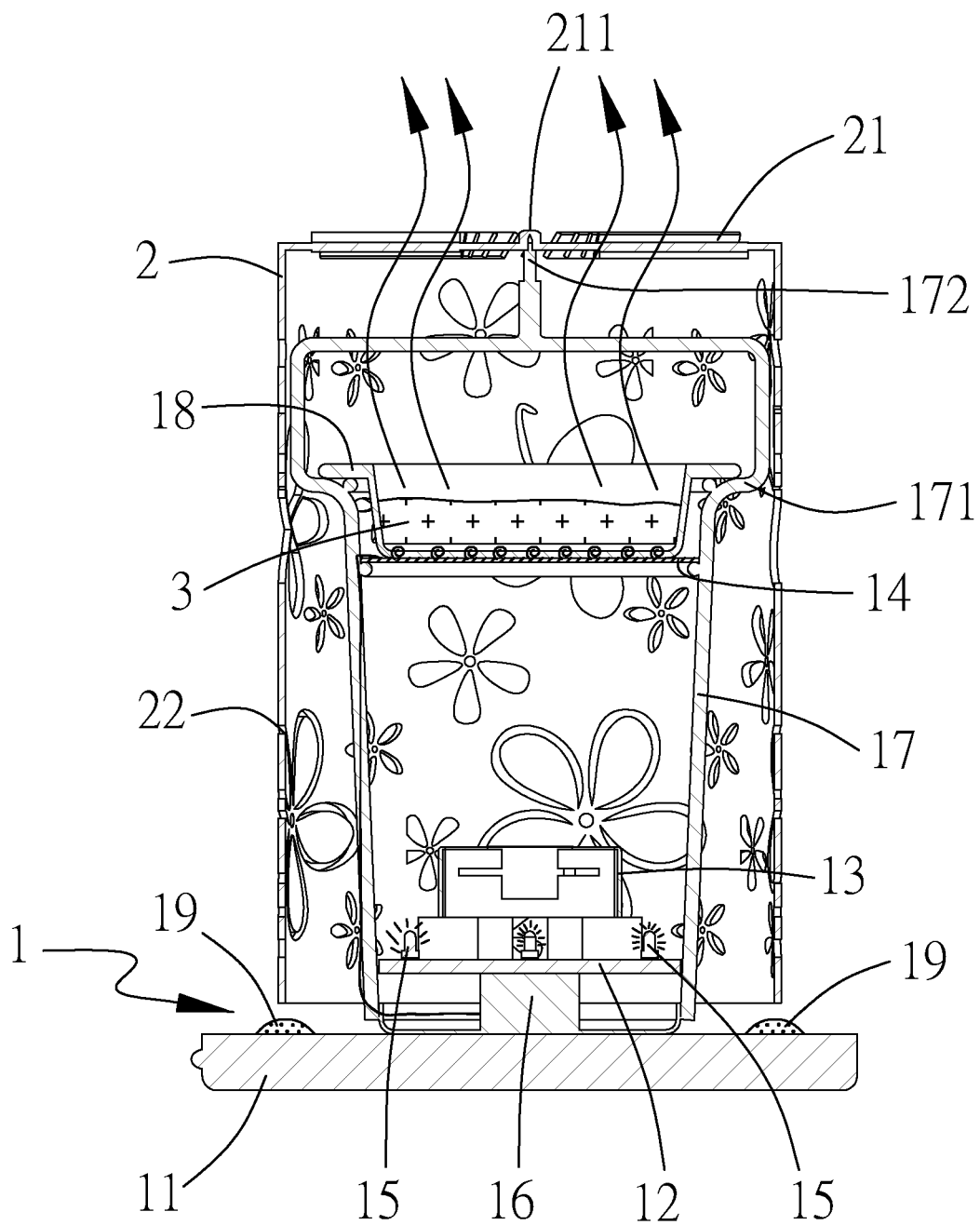
FIG. 3 is a cross-sectional view of the rotary aromatherapy lamp structure of the present invention.

Furthermore, the aromatherapy lamp 1 further includes at least one speaker 19 configured on the base 11 of the aromatherapy lamp 1 or other position thereof as FIG. 3 shows, where the speaker 19 is configured with a control module such as a control circuit in electric with the speaker 19 and electric wire 121; the electric wire 121 is in electric with mains, and the control module then supplies power to the speaker 19, where the control module of the speaker 19 is provided with a Bluetooth transmission function, allowing the speaker 19 to perform audio signal wireless transmission with an external preset multimedia broadcast device such as a smart phone through Bluetooth transmission.

The rotating cover 2 is a hollow body and adapted to cover the base 11 of the aromatherapy lamp 1. The top end of the rotating cover 2 is configured with fan leaves 21 and the bottom thereof is formed with an opening, and the center of the fan leaves 21 is configured with an axle center 211 capable of being a circular hole or a groove outwardly recessed from the inside of the rotating cover 2. The rotating cover 2 is used to cover the control circuit board 21, fan 13, heating element 14, at least one light-emitting element 15, speaker 19 and first support 17, and the fulcrum 172 is adapted to prop against the axle center 211 of the fan leaves 21, allowing a space to be formed between the rotating cover 2 and base 1, and thus allowing the rotating cover 2 to have a rotating mechanism on the aromatherapy lamp 1. Furthermore, the peripheral wall of the rotating cover 2 is opened with a plurality of holes 22, which may be designed to have a variety of patterns.

Figure 4:
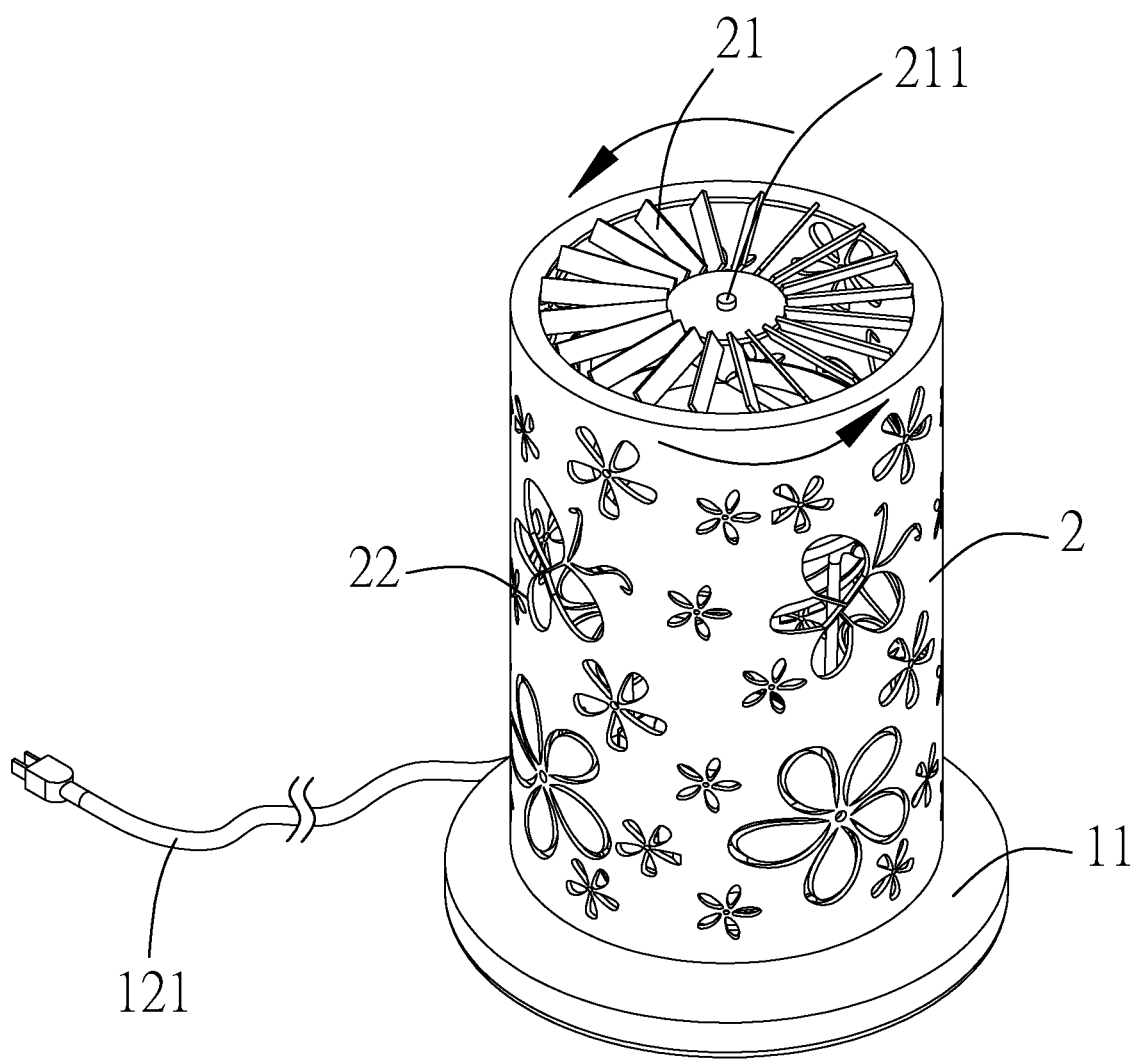
FIG. 4 is a perspective view of the rotary aromatherapy lamp structure of the present invention in a first application state.

When the aromatherapy lamp 1, as FIGS. 3 and 4 show, is used, essential oil 3 is first filled in the container 18 of the aromatherapy lamp 1, and when the control circuit board 12 is powered, the heating element 14 positioned on the bottom of the container 18 is used to heat the essential oil 3 inside the container 18 to speed the evaporation of the essential oil 3, and the air flow generated form the fan 13 can be blown toward the leaves 21 of the rotating cover 2, thereby allowing the rotating cover 2 to have an automatic rotation function so that the flow amount of the air flow can be increased through the rotation of the fan leaves 21 of the rotating cover 2, allowing the volatilized essential oil 3 to be more diffused to indoor space.

In addition, the plurality of holes 22 configured on the peripheral wall of the rotating cover 2 allow the light emitted from the light-emitting element 15 configured on the aromatherapy lamp 1 to penetrate therethrough, allowing the automatic rotation of the rotating cover 2 plus the light of the light-emitting element 15 penetrating through the plurality of holes 22 to make the entire rotary aromatherapy lamp structure more eye-appealing.

Furthermore, the speaker 19 of the aromatherapy lamp 1 can carry out Bluetooth wireless transmission with an external preset multimedia device, allowing a user to carry out audio signal broadcasting at the same time when using aromatherapy lamp 1, thereby promoting the additional value of the aromatherapy lamp 1.

Figure 5:
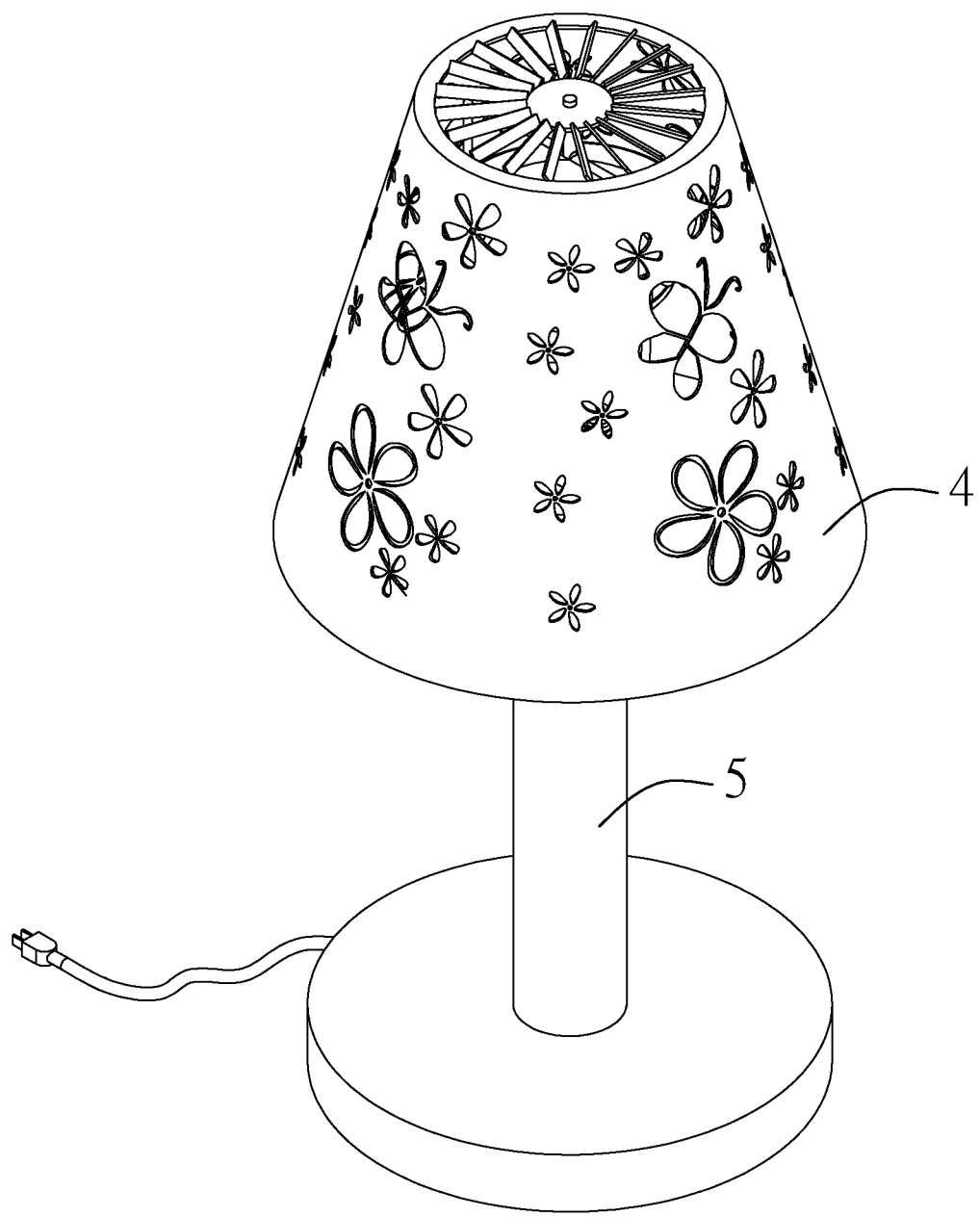
FIG. 5 is a perspective view of the rotary aromatherapy lamp structure of the present invention in a second application state.

Referring to FIG. 5, a lampshade 4 is further covered on the rotating cover 2, and the bottom of the base 11 of the aromatherapy lamp 1 may further in combination with a second support 5, allowing the aromatherapy lamp 1 and rotating cover 2 to be formed into a table lamp through the combination thereof with the lampshade 4 and second support 5, thus further increasing the overall aesthetics and added value of the aromatherapy lamp 1.

I claim:

1. A rotary aromatherapy lamp structure, comprising:
an aromatherapy lamp, comprising a base, control circuit board, fan, light-emitting element and first support, said control circuit board configured on said base and respectively in electric connection with said fan and light-emitting element, surfaces of said fan and base facing toward the same direction, allowing air flow generated from said fan to be blown above said surface of said base, said first support configured on said surface of said base, said first support configured with a mounting portion in combination with a container and positioned relatively above said fan and heating element, said first support further extended with a fulcrum positioned relatively above said container, and said heating element adjacent to a lower position of said container; and
a rotating cover, being a hollow body and adapted to cover said base of said aromatherapy lamp, a top end of said rotating cover configured with fan leaves, and a bottom end thereof formed with an opening, a center of said leaves configured with an axle center, said rotating cover adapted to cover said fan, heating element and first support of said aromatherapy lamp, and said fulcrum of said first support adapted to prop against said axle portion of said fan, allowing a space to be formed between said rotating cover and base.

2. The structure according to claim 1, wherein said aromatherapy lamp further comprises at least one light-emitting element and at least one speaker, said light-emitting element is in electric connection with said control circuit board, and said speaker is in electric connection with a control module having a Bluetooth transmission function.

3. The structure according to claim 2, wherein said control circuit board is in electric connection with an electric wire in electric connection with mains, said control circuit board respectively supplies power to said fan, heating element and light-emitting element, said control module of said speaker is in electric connection with said electric wire, and said control module supplies power to said speaker.

4. The structure according to claim 2, wherein said speaker is configured on said base of said aromatherapy lamp.

5. The structure according to claim 1, wherein a lampshade is further covered on said rotating cover, and a second support is further in combination with a bottom of said base.

6. The structure according to claim 1, wherein a plurality of holes are configured on a peripheral wall of said rotating cover.

7. The structure according to claim 1, wherein said mounting portion is an annular body.

8. The structure according to claim 1, wherein said fulcrum is a tipped body, and said axle center is a groove outwardly recessed from an inner part of said rotating cover.

9. The structure according to claim 1, wherein said fulcrum is a tipped body, and said axle center is a circular hole.

10. The structure according to claim 1, wherein a bottom of said control circuit board is configured with a spacer.

* * * * *